(12) United States Patent
Van Dommelen et al.

(10) Patent No.: US 9,983,122 B1
(45) Date of Patent: May 29, 2018

(54) AQUEOUS SOLUTION CONSTITUENT ANALYZER

(71) Applicant: Sea-Bird Electronics, Inc., Bellevue, WA (US)

(72) Inventors: Ronnie Van Dommelen, Dartmouth (CA); Burkhard Plache, Halifax (CA); Keith Brown, Fall River (CA); Wesley D. Strubhar, Sweet Home, OR (US); Andrew H. Barnard, Corvallis, OR (US); Scott Feener, Laconia (CA)

(73) Assignee: Sea-Bird Electronics, Inc., Bellevue, WA (US)

( * ) Notice: Subject to any disclaimer, the term of this patent is extended or adjusted under 35 U.S.C. 154(b) by 0 days. days.

(21) Appl. No.: 15/667,851

(22) Filed: Aug. 3, 2017

(51) Int. Cl.
*G01J 1/42* (2006.01)
*G01N 21/27* (2006.01)
*G01N 21/33* (2006.01)
*G01N 21/25* (2006.01)
*G01J 3/10* (2006.01)

(52) U.S. Cl.
CPC .............. *G01N 21/274* (2013.01); *G01J 3/10* (2013.01); *G01N 21/255* (2013.01); *G01N 21/33* (2013.01); *G01N 2201/0621* (2013.01); *G01N 2201/12753* (2013.01); *G01N 2201/12792* (2013.01)

(58) Field of Classification Search
CPC .............. G01N 21/64; G01N 15/1012; G01N 2021/062; G01N 2021/06113; G01N 2021/127
See application file for complete search history.

(56) References Cited

U.S. PATENT DOCUMENTS

| 3,826,899 | A | * | 7/1974 | Ehrlich | G01N 15/147 377/10 |
| 5,825,792 | A | * | 10/1998 | Villeneuve | H01S 3/137 372/28 |
| 9,789,508 | B2 | * | 10/2017 | Baumgartner | B05B 17/0607 |
| 2003/0067946 | A1 | * | 4/2003 | Wiemeyer | H01S 3/137 372/29.02 |
| 2005/0073690 | A1 | * | 4/2005 | Abbink | G01J 3/26 356/451 |
| 2014/0203184 | A1 | * | 7/2014 | Purdy | G01N 33/18 250/393 |
| 2015/0160131 | A1 | * | 6/2015 | Kinugasa | G01N 21/64 250/252.1 |
| 2016/0216712 | A1 | * | 7/2016 | Baumgartner | A61L 2/22 |
| 2016/0299441 | A1 | * | 10/2016 | Ahlawat | G03F 7/70575 |

* cited by examiner

*Primary Examiner* — Kiho Kim
(74) *Attorney, Agent, or Firm* — Perkins Coie LLP (57) ABSTRACT

Technology is provided for an aqueous solution constituent analyzer. The analyzer includes an ultraviolet light emitting diode (LED) with a current source providing variable current thereto. A spectrometer is positioned for receiving light from the LED transmitted through an aqueous solution. A controller receives radiant flux data for a plurality of wavelengths and determines, based on the radiant flux data, a usable number of the plurality of wavelengths that satisfies a relative uncertainty threshold. The controller can increase the current to the LED if the usable number of wavelengths is less than a minimum threshold and calculate a concentration of a constituent of interest in the solution. The controller can also determine a peak wavelength of the plurality of wavelengths having the greatest intensity value, and decrease the current level to the LED if the peak wavelength has an intensity value greater than a saturation value for the spectrometer.

23 Claims, 7 Drawing Sheets

AQUEOUS SOLUTION CONSTITUENT ANALYZER

TECHNICAL FIELD

This patent application is directed to aqueous solution constituent measurement systems and, more specifically, to systems for controlling radiation sources for absorption spectroscopy.

BACKGROUND

Nitrate analyzers use absorption spectroscopy to measure dissolved nitrate concentrations in natural waters, such as oceans, lakes, and rivers, often for the purpose of environmental monitoring and research. Absorption spectroscopy makes use of the characteristic of dissolved constituents in water to selectively absorb light. Molecules, ions, and chemical species in solution have unique wavelength-dependent absorption properties that allow the quantification of these dissolved constituents by measuring spectral absorption of the solution. These instruments typically contain a deuterium plasma arc lamp to provide an ultraviolet (UV) radiation source. The analyzer measures the spectral UV radiation transmitted through a water sample and compares this signal with a prior baseline measurement of pure water in order to determine the absorption spectrum of the dissolved constituents (e.g., nitrate) in the sample.

Conventional broadband UV radiation sources such as deuterium and hydrogen discharge lamps suitable for measurement of radiation absorption in aqueous solutions are high power, costly, physically large, slow to stabilize, and the radiation output used for the absorption measurement can only be controlled by lamp pulse width and/or detector integration time. Consequently, instruments using such sources for measuring chemical species dissolved in water with UV absorption, (1) have limited control of radiation output which limits measurement performance in terms of accuracy, precision, sensitivity and range, and (2) require complex control, power electronics, and heat management schemes that make them too complex and expensive to be practical for the environmental monitoring market.

BRIEF DESCRIPTION OF THE DRAWINGS

Embodiments of the aqueous solution constituent analyzers disclosed herein may be better understood by referring to the following Detailed Description in conjunction with the accompanying drawings, in which like reference numerals indicate identical or functionally similar elements.

The headings provided herein are for convenience only and do not necessarily affect the scope or meaning of the claimed embodiments. Further, the drawings have not necessarily been drawn to scale. For example, the dimensions of some of the elements in the figures may be expanded or reduced to help improve the understanding of the embodiments. Moreover, while the disclosed technology is amenable to various modifications and alternative forms, specific embodiments have been shown by way of example in the drawings and are described in detail below. The intention, however, is not to unnecessarily limit the embodiments described. On the contrary, the embodiments are intended to cover all suitable modifications, equivalents, and alternatives falling within the scope of the embodiments as defined by the appended claims.

DETAILED DESCRIPTION

Overview

Aqueous solution constituent analyzers along with systems and methods therefor are disclosed herein. The disclosed analyzers include light emitting diodes (LEDs) rather than traditional deuterium and hydrogen discharge lamps. LEDs are more simply and flexibly operated and are less costly. However, LEDs have a relatively narrow bandwidth (e.g., fewer wavelengths) with a steep bell shape spectrum when compared to traditional light sources. Because of this spectral shape, as absorption increases, the transmitted radiant flux at the outer range of an LED's spectrum rapidly diminishes to below the limit of reliable detection of the spectrometer. Accordingly, the number of wavelengths and therefore equations usable for solving for concentrations is reduced, resulting in poorer quality numerical solutions for constituent concentration. The disclosed technology includes novel hardware design features, control and analysis techniques that account for the LEDs narrow bandwidth, which allows the more simply operated and less costly LEDs to be used to perform in situ measurements of light absorption for identification and quantification of dissolved constituents.

In a representative embodiment, the disclosed analyzer can include a housing defining a sample region and an ultraviolet light emitting diode positioned adjacent the sample region to transmit ultraviolet light through an aqueous solution located in the sample region. A current source can be coupled to the light emitting diode and is operative to output a variable current level to the light emitting diode. A spectrometer can be located in the housing for receiving light transmitted through the aqueous solution and operative to output radiant flux data for each of a plurality of wavelengths transmitted through the aqueous solution. The radiant flux data for each of the plurality of wavelengths includes data indicative of a corresponding intensity value. In some embodiments, a controller is coupled to the current source and the spectrometer and includes instructions for receiving the radiant flux data for each of the plurality of wavelengths and determining, based on the radiant flux data, a usable number of the plurality of wavelengths that satisfies a predetermined relative uncertainty threshold. In some embodiments, the instructions can also include increasing the current level to the light emitting diode if the usable number of wavelengths is less than a minimum usable wavelength threshold, calculating a concentration of a dissolved constituent of interest in the aqueous solution if the usable number of wavelengths is greater than or equal to the minimum usable wavelength threshold, and determining a peak wavelength of the plurality of wavelengths having the greatest intensity value, and decreasing the current level to the light emitting diode if the peak wavelength has an intensity value greater than a predetermined saturation value associated with the spectrometer.

General Description

Various examples of the device and systems introduced above will now be described in further detail. The following description provides specific details for a thorough understanding and enabling description of these examples. One skilled in the relevant art will understand, however, that the techniques discussed herein may be practiced without many of these details. Likewise, one skilled in the relevant art will also understand that the technology can include many other features not described in detail herein. Additionally, some well-known structures or functions may not be shown or described in detail below so as to avoid unnecessarily obscuring the relevant description.

The terminology used below is to be interpreted in its broadest reasonable manner, even though it is being used in conjunction with a detailed description of some specific examples of the embodiments. Indeed, some terms may even be emphasized below; however, any terminology intended to be interpreted in any restricted manner will be overtly and specifically defined as such in this section.

Figure 1A:
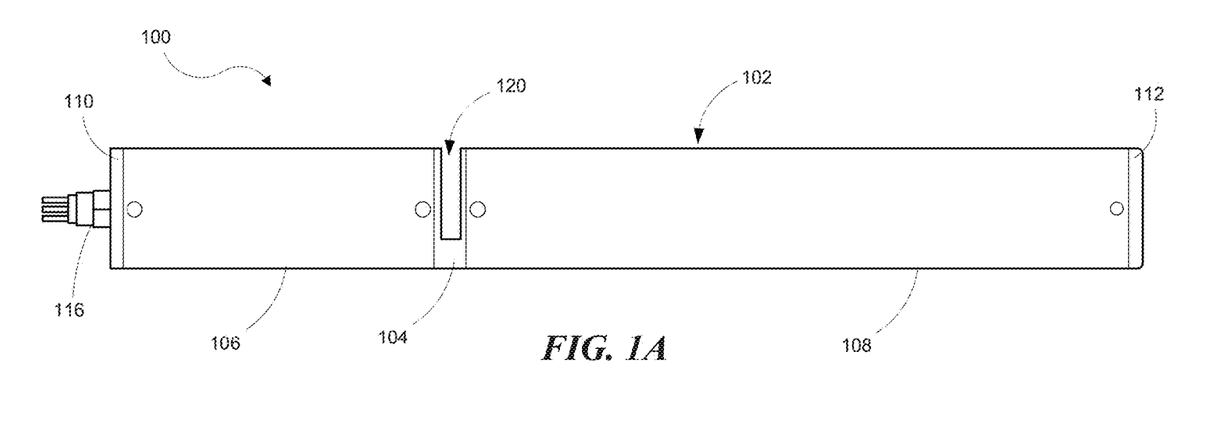
FIG. 1A is a side view of an aqueous solution constituent analyzer according to a representative embodiment.
Figure 1B:
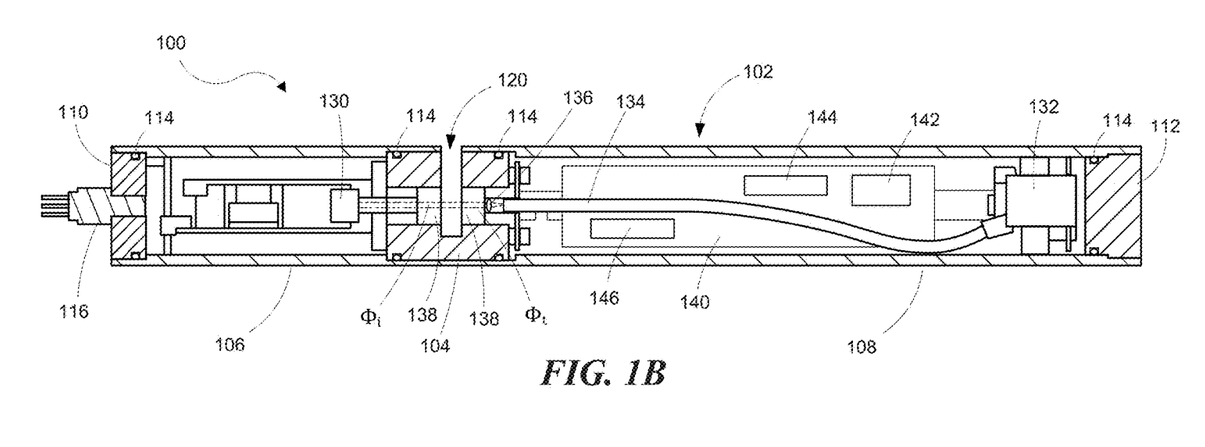
FIG. 1B is a side view in cross-section of the aqueous solution constituent analyzer shown in FIG. 1A.

FIGS. 1A and 1B, illustrate an aqueous solution constituent analyzer 100 according to a representative embodiment of the disclosed technology. The analyzer 100 uses absorption spectroscopy to measure dissolved constituents, such as nitrate, in aqueous solutions including oceans, lakes, and rivers, for example. The analyzer 100 contains a UV LED 130 as a radiation source, a spectrometer 132 as the detector, an open water sample chamber 104 defining a sample region 120, and an electronic controller 140, contained within a metal pressure housing 102 to allow deployment of the instrument in rugged field conditions and at great water depth.

In a representative embodiment, the housing 102 can include the sample chamber 104 with first and second cylindrical housing tubes 106 and 108 coupled thereto. The open ends of the housing tubes 106 and 108 can be closed with corresponding first and second end caps 110 and 112. These components can be joined with cooperative threaded joints and/or welded joints, for example. These joints can be sealed with suitable elastomeric seals, such as O-rings 114, for example. In some embodiments, a bulkhead connector 116 can extend into the first end cap 110 to provide power and communication to the analyzer 100.

The sample chamber 104 can comprise a cylindrical body with a notch extending through a portion of the body to define the sample region 120. Thus, when the analyzer 100 is submerged, the solution to be tested (e.g., aqueous solution sample) fills the sample region 120. The sample chamber 104 includes windows 138 positioned on both sides of the sample region 120 to allow UV radiation from the UV LED 130 (e.g., incident radiant flux $\varphi_i$) to be transmitted into the sample region 120 and through the aqueous solution sample. In some embodiments, the UV LED 130 can be located in the first housing tube 106 adjacent the sample region 120 and the spectrometer 132 can be located in the second housing tube 108. Thus, the UV LED 130 and the spectrometer 132 can be positioned on opposite sides of the sample chamber 104. In some embodiments, the UV radiation that is not absorbed by the sample (transmitted radiant flux $\varphi_t$) is transmitted from the sample region 120 to the spectrometer 132 via a fiber optic cable 134. In some embodiments, a lens 136 can be positioned adjacent the sample region 120 (e.g., next to window 138) to focus the transmitted radiant flux $\varphi_t$ into the fiber optic cable 134. In some embodiments, the lens 136 can be positioned adjacent the sample region 120 (e.g. next to window 138) to focus the transmitted radiant flux $\varphi_t$ directly into the spectrometer 132. In still other embodiments, the transmitted radiant flux $\varphi_t$ travels through the window 138 and into the spectrometer 132.

The electronic controller 140 can be located in the second housing tube 108 and electronically coupled to the spectrometer 132 and a current source 146, which is in turn electronically coupled to the UV LED 130. The controller 140 can include one or more microcontrollers or microprocessors 142 and one or more memory devices 144 for storing instructions and transmitted/received data, for example. The spectrometer 132 is operative to output radiant flux data for each of a plurality of detected wavelengths which can be stored on the one or more memory devices 144 to be used in calculations performed by the microprocessor 142, for example. The current source 146 is operative to output a variable current level to the UV LED 130, thereby varying the intensity of the incident radiant flux $\varphi_i$ and ultimately the transmitted radiant flux $\varphi_t$. In some embodiments, the current source 146 is part of the controller 140 and in other embodiments, the current source 146 can be a separate module located in either the first or second housing tubes 106/108. In some embodiments, the analyzer 100 can include multiple LEDs of varying spectral ranges. In some embodiments where multiple LEDs are provided, the analyzer 100 can provide independent current control of the multiple LEDs to maximize the available spectral channels according to the disclosed technology. Accordingly, the analyzer 100 can include more than one current source.

Figure 2:
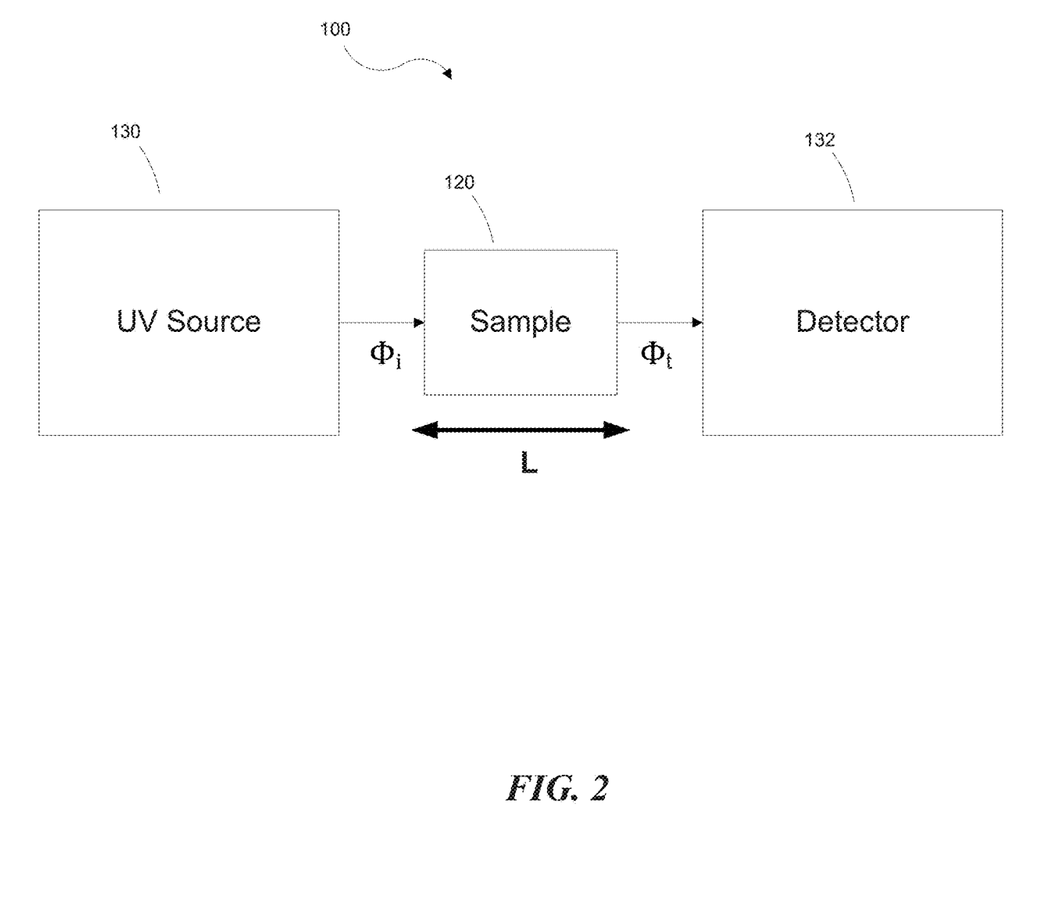
FIG. 2 is a high level schematic representation of an aqueous solution constituent analyzer.

With reference to FIG. 2, UV radiation from the UV source 130 (e.g., UV LED 130 in FIG. 1B) incident on the sample (i.e., $\varphi_i$) is partially absorbed over the sample path length L. The transmitted UV radiation (i.e., $\varphi_t$) is measured by the detector 132 (e.g., spectrometer 132 in FIG. 1B). Absorption spectroscopy makes use of the characteristic of dissolved constituents in water to absorb light selectively. Molecules, ions, and chemical species in solution have unique wavelength dependent absorption properties that allow the quantification of these dissolved constituents by measuring spectral absorption of the solution. The analyzer 100 measures the spectral UV radiation transmitted through the water sample (i.e., transmitted radiant flux $\varphi_t$) via detector 132 and compares this signal with a prior baseline measurement of pure water in order to determine the absorption spectrum of the dissolved constituents in the sample. The analyzer 100 can be calibrated with pure water, zero nitrate seawater, and/or aqueous solutions of known nitrate concentrations, for example. As explained more fully below, the analyzer 100 can apply the Beer-Lambert law, using multi-variable linear regression to calculate a best estimate of nitrate concentration. Although the disclosure describes the analyzer 100 and its operation with respect to nitrate analysis, the analyzer 100 can be configured and/or calibrated to measure the concentrations of other dissolved substances. Furthermore, although the disclosure describes the analyzer 100 with respect to UV LEDs, other LEDs having different output spectrums can be used.

The quality of the analyte concentration calculation depends on having a sufficient number of wavelength channels over a spectral range containing the characteristic absorption spectrum of the chemical species of interest where the transmitted radiant flux $\varphi_t$ measurements have satisfactory (e.g., low) relative uncertainty. Data points of high uncertainty result in the numerical solution of the system of equations becoming unstable, and therefore are omitted from the solution.

As mentioned above, the UV LED 130 can have a relatively narrow bandwidth with a steep bell shape spectrum. The bandwidth is specified as the Full Width Half Maximum, and is of the order of 10-20 nm. Because of this spectral shape, as absorption increases, the transmitted radiant flux $\varphi_t$ at the outer range of the UV LED spectrum rapidly diminishes to below the limit of detection of the spectrometer, or if not, then to levels where the relative uncertainty is unacceptable. The number of wavelengths and therefore equations usable for solving for concentrations is reduced, resulting in poorer quality numerical solutions for the concentration of chemical species ($c_s$).

The disclosed aqueous solution constituent analyzer 100 uses analysis and control techniques to compensate for the narrow spectral band of the UV LED 130 compared to other UV radiation sources. Referring to the system diagram of FIG. 3, the controller 140 increases the UV LED 130 output, which is the product of radiant flux, $\varphi_i(\lambda)$, and pulse width, t, (and correspondingly the detector integration time), in response to the loss of usable wavelength channels due to high absorption in sample volume 120. The controller 140 can use closed loop control techniques to adjust the UV LED output and detector integration time t to maximize the number of usable wavelength channels without saturating any wavelength channels. The control logic can include hysteresis to ensure the response is damped appropriately. In some embodiments, the control logic can use other closed loop control techniques, such as proportional, integral, derivative (PID) controls, for example.

Figure 3:
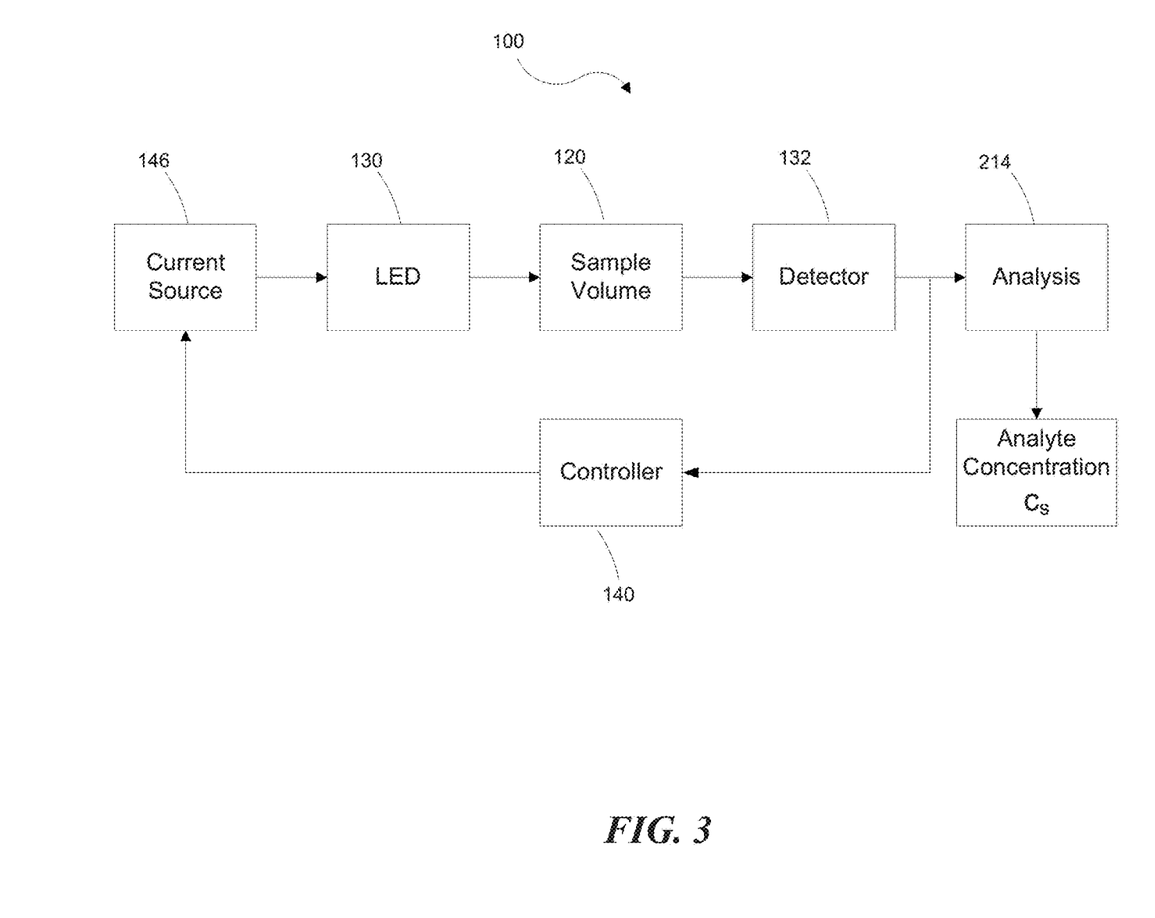
FIG. 3 is a schematic representation of an aqueous solution constituent analyzer system.

In some embodiments, the increase in incident radiant flux, $\varphi_i(\lambda)$ (e.g., UV LED output), is accomplished by increasing the current level (e.g., forward current, $I_f$) supplied from the current source 146 to the UV LED 130. The controller 140 increases LED output when the number of usable wavelength channels measured by the spectrometer 132 is insufficient to produce a high quality numerical solution for the concentration of dissolved constituents, $c_s$. When the number of usable wavelength channels measured by the spectrometer 132 is sufficient, the system performs an analysis 214 on the radiant flux data received from the spectrometer 132 to determine the concentration of dissolved constituents, $c_s$. In some embodiments, the analysis 214 is performed by the controller 140, and in other embodiments the radiant flux data can be transmitted to another device to perform the analysis.

Controlling the LED pulse width t and detector integration time modulates the duration of the measurement. In some embodiments, the analyzer 100 uses a calibration table (e.g., look-up table) that relates LED current level and pulse width/integration time to the resulting radiation incident on the sample. In other embodiments, the relationship of the LED current level and pulse width/integration time is calculated from a few calibrated data points.

The detector 132 (e.g., spectrometer 132 in FIG. 1B) is capable of measuring radiant flux, $\varphi(\lambda)$, over a given signal strength range determined by its inherent characteristics. When the radiant flux exceeds the maximum limit of the detector, the detector is said to be saturated. The detector also has a characteristic sensitivity, the ability to measure low levels of radiant flux, $\varphi(\lambda)$, down to a limit of detection, reached when the response of the detector is just discernible from its response to darkness, i.e., zero radiant flux, known as the dark noise or the noise floor. The limit of detection is greater than the noise floor. When the response of the detector is at the level of the noise floor, the radiant flux signal is not discernible.

Figure 4:
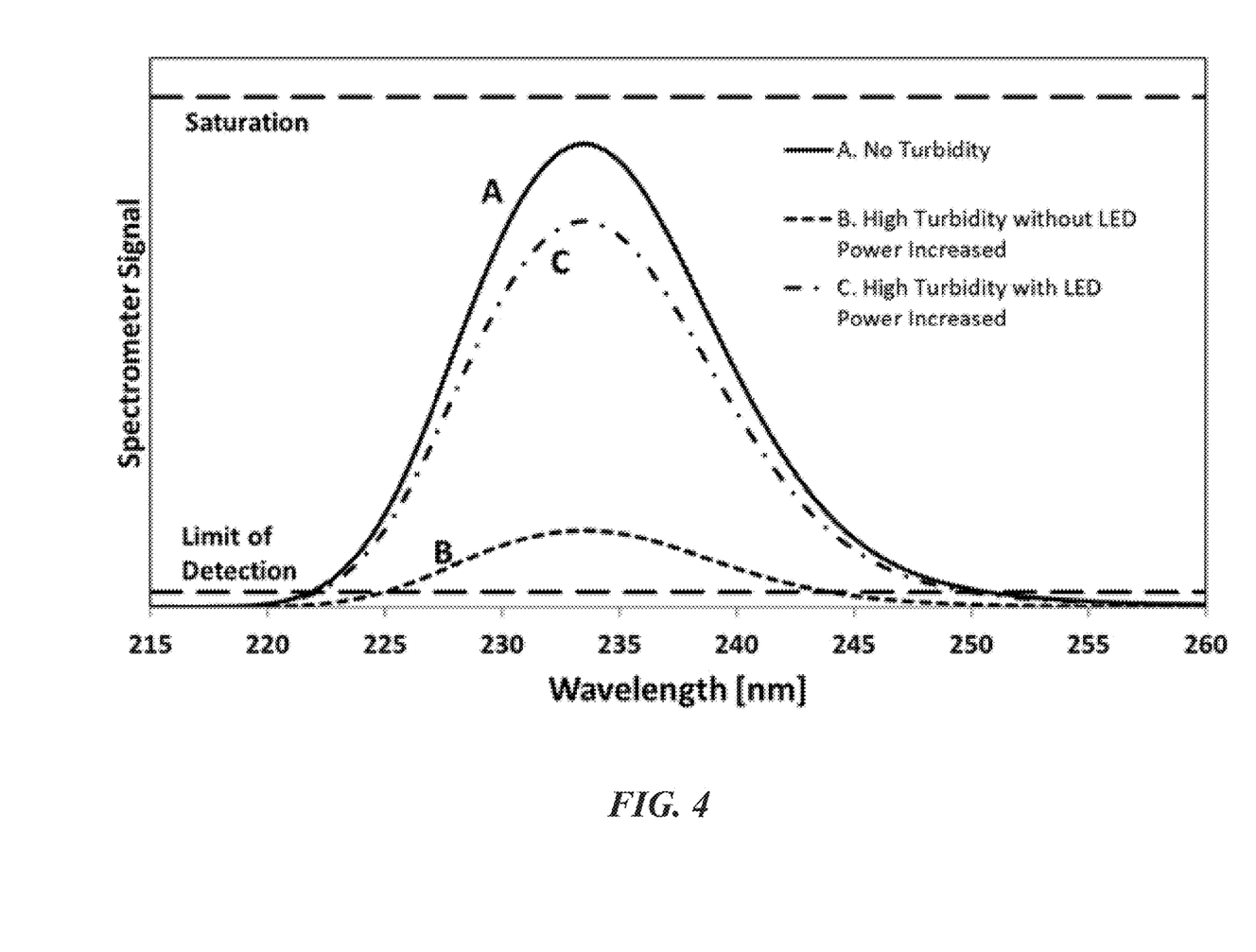
FIG. 4 is a graph illustrating the effect of turbidity on measured spectrum.

As absorption increases, the transmitted radiant flux, $\varphi_t(\lambda)$, decreases differentially across wavelengths depending on the constituents of the sample. For some wavelengths the transmitted radiant flux, $\varphi_t(\lambda)$, approaches or passes below the limit of detection. Absorption may be due to an interfering species in the sample, such as a broadband absorber like turbidity. As shown in FIG. 4, when no turbidity is present, the spectrometer signal A is strong and provides usable wavelengths between approximately 223-248 nm. However, with high turbidity, the spectrometer signal B is weak and provides useable wavelengths between approximately 228-240 nm. Increasing the current level supplied to the UV LED 130 brings the spectrometer signal C back up to a level that provides almost as many usable wavelengths as if no turbidity was in the sample.

Figure 5:
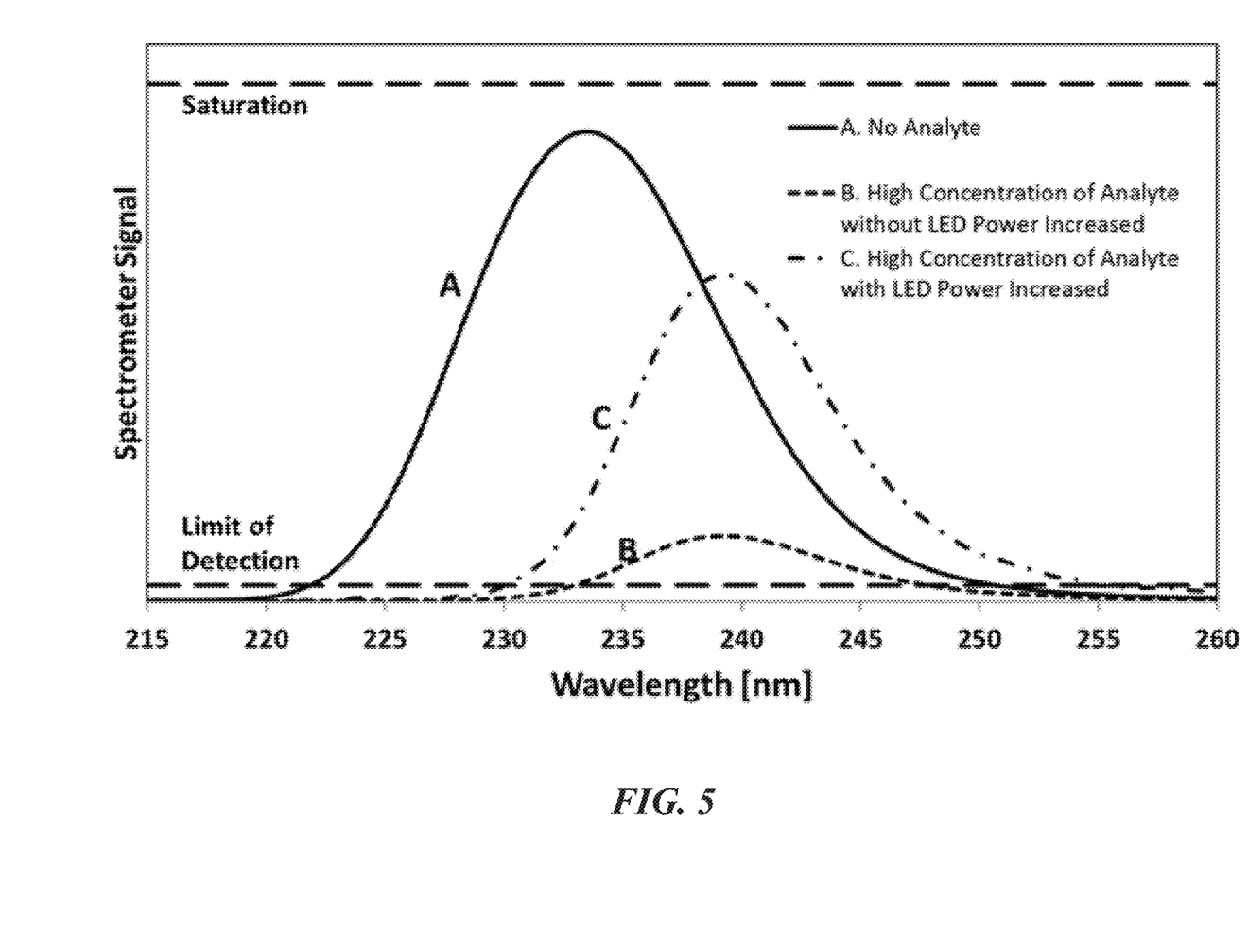
FIG. 5 is a graph illustrating the effect of an analyte on measured spectrum.

In other cases, absorption may be due to a high concentration of an analyte with a characterised absorption spectrum, such as nitrate. As shown in FIG. 5, when no analyte is present, the spectrometer signal A is strong and provides usable wavelengths between approximately 224-248 nm. However, with high analyte concentration, the spectrometer signal B is weak and provides useable wavelengths between approximately 235-245 nm. Increasing the current level supplied to the UV LED 130 brings the spectrometer signal C back up to a level that provides an acceptable number of usable wavelengths, approximately between 232-251 nm. It should be noted that the wavelength shift in the spectrometer signal between A and (B or C) is due to the selective absorptive properties of the analyte in the sample. In contrast, turbidity (FIG. 4) is a broadband absorber that generally absorbs all of the wavelengths.

Figure 6:
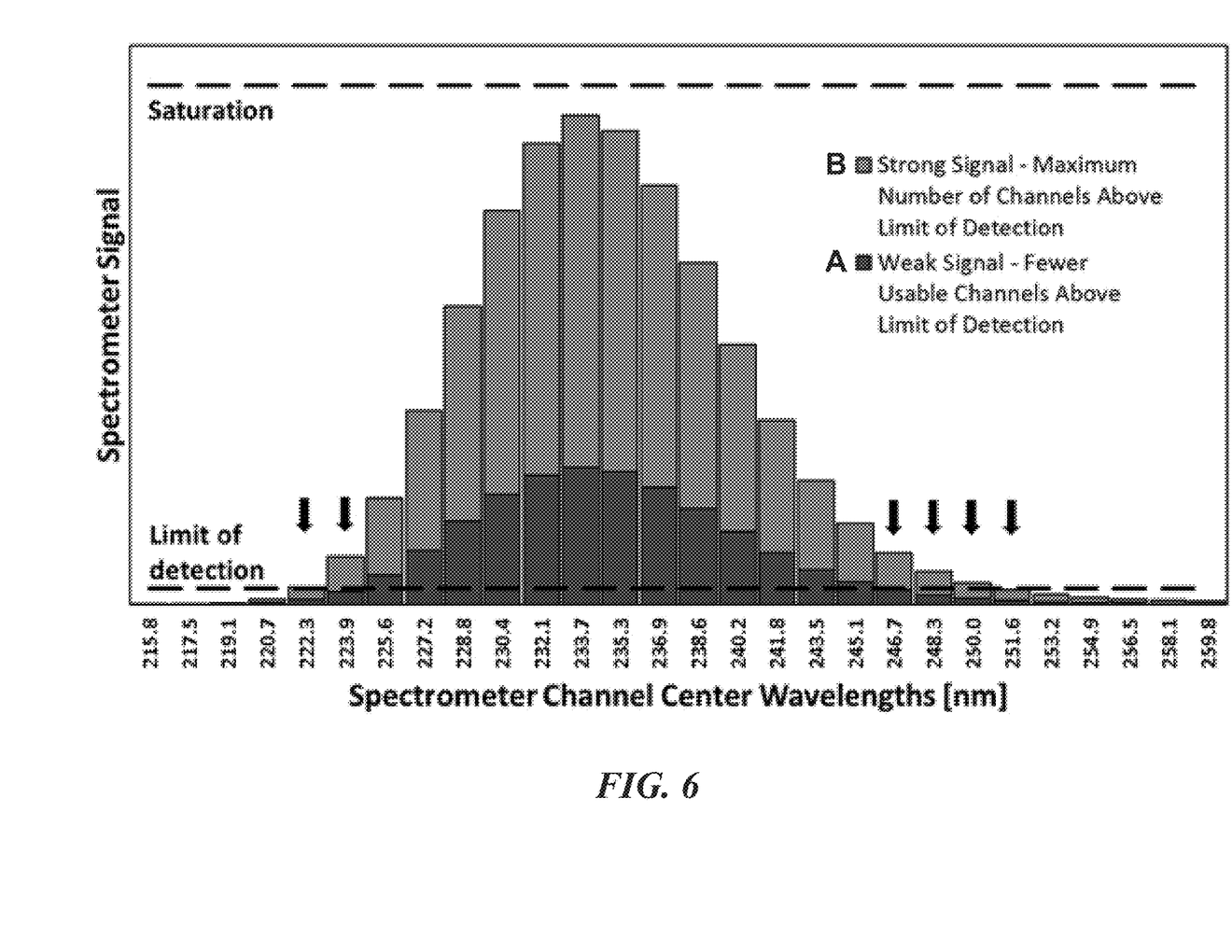
FIG. 6 is a graph illustrating the spectrum observed as discrete wavelength channels of the spectrometer.

FIG. 6 illustrates the difference in usable wavelengths between strong and weak spectrometer signals in terms of discrete wavelength channels of the spectrometer. Each channel is generally centered on a particular wavelength. The weak signal A has 13 usable channels whereas the strong signal B has 19 usable channels. The strong signal B has more useable channels due to an increase in the current level supplied to the UV LED 130. The difference between the strong and weak signals (indicated with six arrows) represents a significant difference of approximately 46 percent.

The number of wavelength channels that are usable in the numerical solution of the system of equations depends on the transmitted radiant flux, $\varphi_t(\lambda)$, falling within the measurement range of the detector, greater than the limit of detection, less than the saturation limit, and having a satisfactory relative uncertainty.

The relative uncertainty of transmitted radiant flux at wavelength $\lambda$ is the spectrometer's uncertainty, $\delta\varphi_t(\lambda)$, divided by the measured transmitted radiant flux at wavelength $\lambda$, $\varphi_t(\lambda)$.

$$\frac{\delta\phi t(\lambda)}{\phi t(\lambda)} \text{Relative Uncertainty (unitless)}$$

This value drives the uncertainty in the left hand side of the Beer-Lambert equation, and therefore the stability of the numerical solution for, $c_s$.

The spectrometer's uncertainty of transmitted radiant flux can be a manufacturer specified value that sometimes corresponds to the dark noise or the noise floor of the spectrometer. In some embodiments, this value can be measured in calibration.

$\delta\varphi_t(\lambda)$ Spectrometer uncertainty of transmitted radiant flux at wavelength, $\lambda$, in mW/nm.

The maximum allowed transmitted radiant flux relative uncertainty is used as the channel rejection criterion to reject wavelength channels from the numerical determination of concentration, $c_s$, to ensure a stable, reliable result.

$$\frac{\delta\phi t(\lambda)}{\phi t(\lambda)}\text{max Channel rejection criterion}$$

The channel rejection criterion is a predetermined relative uncertainty threshold that can be determined experimentally to result in a specified level of accuracy in $c_s$.

A minimum usable channel criterion is used to ensure that a minimum number of wavelength channel data points are used in the numerical determination of concentration, $c_s$. The minimum usable wavelength channel criterion or threshold can be determined experimentally to result in a specified level of accuracy in $c_s$.

If increasing the UV LED output results in the transmitted radiant flux, $\varphi_t(\lambda)$, saturating any of the wavelength channel detectors, then the controller reduces the UV LED output by reducing either the current, $I_f$, applied to the UV LED, or the UV LED pulse width and detector integration time, or both. The spectrometer's $\varphi_{saturation}$ value can be a predetermined saturation value associated with the spectrometer which is provided by the spectrometer's manufacturer and/or determined through calibration.

Figure 7:
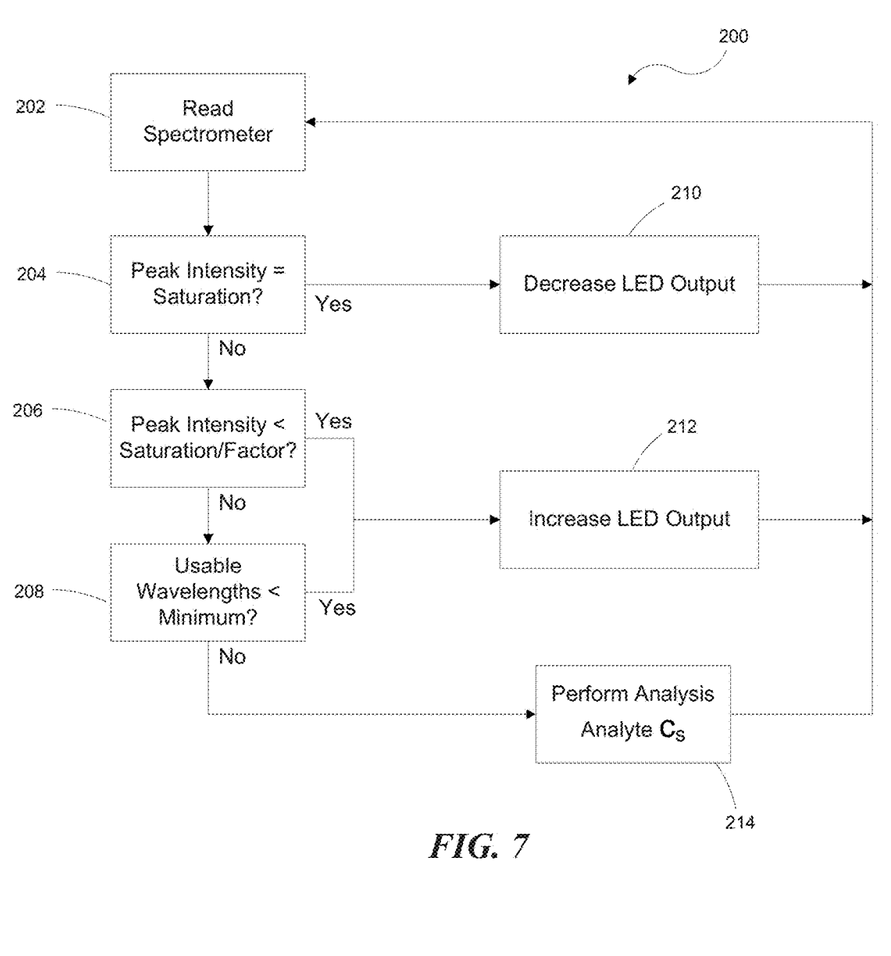
FIG. 7 is a flow chart illustrating representative steps for controlling an aqueous solution constituent analyzer.

With reference to FIG. 7, the analyzer 100 can include instructions for implementing system logic 200, according to a representative embodiment. In some embodiments the system logic 200 can include reading the spectrometer 132 and receiving the radiant flux data for each of a plurality of wavelengths into the controller 140 at step 202. In some embodiments, the radiant flux data includes data indicative of a corresponding transmitted flux intensity value for each wavelength.

At step 204 the controller determines a peak wavelength of the plurality of wavelengths having the greatest intensity value. If the peak wavelength has an intensity value greater than or equal to a predetermined saturation value ($\varphi_{saturation}$) associated with the spectrometer, the controller decreases the output of the UV LED 130 at step 210, by decreasing the current level to the UV LED 130, for example.

If $\varphi_t(\lambda_{peak}) \geq \varphi_{saturation}$ then decrease UV LED current and/or pulse width and detector integration time.

At step 206 the controller 140 determines if the peak wavelength has an intensity value less than the predetermined saturation value divided by a selected factor. If the peak wavelength has an intensity value less than the predetermined saturation value divided by a selected factor, the controller increases the output of the UV LED 130 at step 212, by increasing the current level to the UV LED 130, for example. In at least one embodiment the selected factor can be 0.5.

If $\varphi_t(\lambda_{peak}) < 0.5 \cdot \varphi_{saturation}$ then increase UV LED current and/or increase the pulse width and detector integration time.

At step 208 the controller determines, based on the radiant flux data, a usable number of the plurality of wavelengths that satisfies the predetermined relative uncertainty threshold. The usable number of the plurality of wavelengths includes calculating a relative uncertainty value for each of the plurality of wavelengths by dividing the intensity value for each of the plurality of wavelengths by the predetermined uncertainty value associated with the spectrometer and comparing the relative uncertainty value with the predetermined relative uncertainty threshold.

If $$\frac{\delta\phi t(\lambda)}{\phi t(\lambda)} < \frac{\delta\phi t(\lambda)}{\phi t(\lambda)}\text{max}$$

then wavelength channel is usable

If the usable number of wavelengths ($\lambda_{Usable}$) is less than the minimum usable wavelength threshold, the controller 140 can increase the output of the UV LED 130 at step 212, by increasing the current level to the UV LED 130, for example.

If $\lambda_{Usable}$<minimum usable wavelength threshold then increase UV LED current and/or increase the pulse width and detector integration time.

When setting UV LED current and/or pulse width and detector integration time, the control logic calculates inputs to maximize use of the dynamic range of the detector, for example, so that the highest transmitted radiance flux of any wavelength would be close to the saturation limit, e.g., Set [$I_f$, t] so that $\varphi_t(\lambda_{peak}) \cong 0.9 \cdot \varphi_{saturation}$ Modulation of the current, and therefore of the incident radiant flux emitted by the UV LED, and of the pulse width and integration time may be continuous or in discrete steps. For each current level and pulse width/integration time, the calibration data may be processed to produces a record of $\varphi_t(\lambda, I_f, t)$. The control logic can include hysteresis to ensure the response is damped appropriately.

Once the usable number of wavelengths ($\lambda_{Usable}$) is greater than the minimum usable wavelength threshold, the concentration of analyte can be calculated at step 214 as follows:

The absorption of light in a medium is described by the Beer-Lambert Law, $$A(\lambda) = \log 10\left(\frac{\phi i(\lambda)}{\phi t(\lambda)}\right) = L\sum_{s=1}^{m} c_s \varepsilon_s(\lambda)$$

Where the parameters are defined as follows, $\lambda$ wavelength of the UV, visible light, or IR radiation, in nm, $A(\lambda)$ Absorption, a unit-less value, at wavelength, $\lambda$, $\varphi_i(\lambda)$ Incident radiant flux at wavelength, $\lambda$, in mW/nm, $\varphi_t(\lambda)$ Transmitted radiant flux at wavelength, $\lambda$, in mW/nm, L Path length through the aqueous solution sample, in cm, $c_s$ Concentration of chemical species, s, in molarity units, M, and $\varepsilon_s(\lambda)$ Absorptivity coefficient of chemical species, s, in $M^{-1} cm^{-1}$ at wavelength, $\lambda$, m Number of chemical species in the solution.

This means that absorption is additive, and for each constituent, absorption is linearly proportional to its concentration.

The radiant flux may be measured using a spectrometer that has an array of detector elements or channels each of which detects light over a narrow spectral band. The spectral bands of the detector array span the spectrum of interest.

Each detector channel is named for its center wavelength and is indexed from the shortest wavelength to the longest wavelength in the spectrometer spectral range as $\lambda_1, \lambda_2, \lambda_3, \ldots \lambda_n$. The number of channels used for the measurement is denoted as n Number of wavelength channels It is possible to control and vary the sample path length, L (FIG. 2), to adapt this measurement technique for changing absorption conditions, and the present technology is applicable for such implementations. However, for simplicity of the discussion, but not to limit the application of this technology, the path length, L, is assumed to be fixed, and the path length and absorptivity coefficient, $\epsilon$, are combined into one parameter, called the extinction coefficient, E. The extinction coefficient is a wavelength dependent characteristic of the absorptivity of the species dissolved in the aqueous solution and the path length through it, as specified in the following equation:

$$E_s(\lambda) = L\epsilon_s(\lambda)$$

where $E_s(\lambda)$ Extinction coefficient of chemical species, s, at wavelength, $\lambda$, in inverse molarity units, $M^{-1}$.

Concentrations of dissolved constituents are determined by solving a set of the following equation for wavelengths, $\lambda_1, \lambda_2, \lambda_3, \ldots \lambda_n$, for concentrations, $c_1, c_2, c_3, \ldots c_m$.

$$\log 10\left(\frac{\phi i(\lambda)}{\phi t(\lambda)}\right) = c_1 E_1(\lambda) + c_2 E_2(\lambda) + c_3 E_3(\lambda) + \ldots$$

where the other terms are found as follows:

$\varphi_i(\lambda)$, incident radiant flux at wavelengths, $\lambda_1, \lambda_2, \lambda_3, \ldots \lambda_n$, is determined during calibration by measuring the transmitted radiant flux through a sample of pure water, i.e. where $c_s=0$, for all s;

$E_s(\lambda)$, the extinction coefficients for chemical species, s, at wavelengths, $\lambda_1, \lambda_2, \lambda_3, \ldots \lambda_n$, are determined during calibration by measuring the transmitted radiant flux through a standard aqueous solution of chemical species, s, of known concentration, $c_s$; and $\varphi_t(\lambda)$, the transmitted radiant flux at wavelengths, $\lambda_1, \lambda_2, \lambda_3, \ldots \lambda_n$, is measured directly by the spectrometer.

For a spectrometer with n wavelength channels, there are n equations to solve for one or more constituent concentrations, $c_s$. When the number of constituent concentrations, m, is less than n, this is an overdetermined system, having more equations than unknowns. In practice a sample of water from a natural source contains other unidentified or uncharacterized UV absorbers for which extinction coefficients are unknown. Such constituents are referred to as interfering species. The system of equations cannot be solved by the standard algebra approach of substitution and elimination. It may be solved for the best estimate of $c_s$ by a variety of numerical techniques, such as linear least squares. From the foregoing it can be appreciated that, as mentioned above, the quality of the result depends on having a sufficient number of wavelength channels over a spectral range containing the characteristic absorption spectrum of the chemical species of interest where the transmitted radiant flux measurements have satisfactory relative uncertainty.

In some embodiments, the UV LED 130 is operated over a finite range of forward current, $I_f$, for example 5-100 mA, determined by inherent limitations of the LED, and selected to achieve good operational characteristics such as stability, linearity, energy efficiency, and operating life. In some embodiments, the UV LED 130 is also operated over a finite range of pulse width, t, corresponding to a range of detector integration time, t, for example 5-5000 ms, determined by inherent limitations of the LED and the detector, and selected to achieve good operational characteristics such as stability, low noise, time response, and energy efficiency.

In some embodiments the analyzer 100 can be calibrated across the following variables: UV LED forward current, $I_f$; UV LED pulse width and detector integration time, t; wavelength; and analyte concentrations, for example. In some embodiments, the instrument may be characterized for other environmental factors such as temperature and pressure.

In various embodiments, the analyzer 100 can use one or more of the following: one or more UV LEDs of one or more nominal wavelengths; UV LEDs with nominal peak wavelengths in the range 220 nm-380 nm; UV LEDs with full width half maximum bandwidths in the range 10-30 nm; UV LED drive current in the range 5-100 mA; and/or pulse widths and detector integration times in the range 5-5000 ms.

In various embodiments, the analyzer 100 is applicable in systems using any suitable type of UV photonic detector such as: spectrometers with a large number of channels with fine wavelength resolution, for example 20-2048 channels with 0.5-10 nm resolution; small number of discrete detectors with course wavelength resolution, for example 2-10 channels with 5-20 nm resolution; a single detector responding to the full or a partial spectral band of the UV source.

One feature of analyzers having configurations in accordance with embodiments described above is that, compared to other UV light sources, UV LEDs use less power, are less costly, smaller, more stable on sampling timescales, and have controllable radiant flux. An advantage of this arrangement is that the mechanical, electrical, control and processing logic, thermal management and optical components to support the UV LED are simpler and less costly than the prior art. Flexible control of radiation output improves the operating range and accuracy with respect to the measured quantity and the presence of interfering species that absorb UV radiation.

Improved performance in particularly high absorbing conditions will grow the market for challenging riverine and agriculture impacted environments. The lower cost instrument will unlock pent up demand for nitrate sensors for operational environmental monitoring. Lower maintenance costs will free up budget for more sensors. Lower power requirements will simplify operation and enhance ease of use when the instrument is integrated with common data loggers. The instrument expands the market from the domain of scientific research and environmental spot sampling to becoming a standard sensor in aquatic environmental monitoring suites.

Remarks

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer, a microprocessor, processor, and/or microcontroller (or other electronic devices) to perform a process. The machine-readable medium may include, but is not limited to, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. It will be appreciated that the same thing can be said in more than one way. Consequently, alternative language and synonyms may be used for any one or more of the terms discussed herein, and any special significance is not to be placed upon whether or not a term is elaborated or discussed herein. Synonyms for some terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification. Unless otherwise defined, all technical and scientific terms used herein have the same meaning as commonly understood by one of ordinary skill in the art to which this disclosure pertains. In the case of conflict, the present document, including definitions, will control.

What is claimed is:

1. An aqueous solution constituent analyzer, comprising:
    a housing defining a sample region;
    a light emitting diode positioned adjacent the sample region to transmit light through an aqueous solution located in the sample region;
    a current source coupled to the light emitting diode and operative to output a variable current level to the light emitting diode;
    a spectrometer positioned in the housing to receive light transmitted through the aqueous solution and operative to output radiant flux data for each of a plurality of wavelengths transmitted through the aqueous solution; and
    a controller coupled to the current source and the spectrometer and including instructions for:
        receiving the radiant flux data for each of the plurality of wavelengths;
        determining, based on the radiant flux data, a usable number of the plurality of wavelengths that satisfies a predetermined relative uncertainty threshold; and
        increasing the current level to the light emitting diode when the usable number of wavelengths is less than a minimum usable wavelength threshold.

2. The aqueous solution constituent analyzer of claim 1, wherein the light emitting diode is an ultraviolet light emitting diode.

3. The aqueous solution constituent analyzer of claim 1, wherein the radiant flux data for each of the plurality of wavelengths includes data indicative of a corresponding intensity value.

4. The aqueous solution constituent analyzer of claim 3, wherein determining the usable number of the plurality of wavelengths includes calculating a relative uncertainty value for each of the plurality of wavelengths by dividing the intensity value for each of the plurality of wavelengths by a predetermined uncertainty value associated with the spectrometer and comparing the relative uncertainty value with the predetermined relative uncertainty threshold.

5. The aqueous solution constituent analyzer of claim 3, further comprising instructions for determining a peak wavelength of the plurality of wavelengths having the greatest intensity value, and decreasing the current level to the light emitting diode when the peak wavelength has an intensity value greater than a predetermined saturation value associated with the spectrometer.

6. The aqueous solution constituent analyzer of claim 5, further comprising instructions for increasing the current level to the light emitting diode when the peak wavelength has an intensity value less than the predetermined saturation value divided by a selected factor.

7. The aqueous solution constituent analyzer of claim 1, further comprising instructions for calculating a concentration of a dissolved constituent of interest in the aqueous solution when the usable number of wavelengths is greater than or equal to the minimum usable wavelength threshold.

8. The aqueous solution constituent analyzer of claim 7, wherein the constituent of interest comprises nitrate.

9. The aqueous solution constituent analyzer of claim 1, wherein the controller includes at least one microprocessor and at least one memory device for storing the instructions.

10. An aqueous solution constituent analyzer, comprising:
    a housing defining a sample region;
    an ultraviolet light emitting diode positioned adjacent the sample region to transmit ultraviolet light through an aqueous solution located in the sample region;
    a current source coupled to the light emitting diode and operative to output a variable current level to the light emitting diode;
    a spectrometer positioned in the housing to receive light transmitted through the aqueous solution and operative to output radiant flux data for each of a plurality of wavelengths transmitted through the aqueous solution, wherein the radiant flux data for each of the plurality of wavelengths includes data indicative of a corresponding intensity value; and
    a controller coupled to the current source and the spectrometer, the controller including at least one microprocessor and at least one memory device to store instructions for:
        receiving the radiant flux data for each of the plurality of wavelengths;
        determining, based on the radiant flux data, a usable number of the plurality of wavelengths that satisfies a predetermined relative uncertainty threshold;

increasing the current level to the light emitting diode when the usable number of wavelengths is less than a minimum usable wavelength threshold;

calculating a concentration of a dissolved constituent of interest in the aqueous solution when the usable number of wavelengths is greater than or equal to the minimum usable wavelength threshold; and determining a peak wavelength of the plurality of wavelengths having the greatest intensity value, and decreasing the current level to the light emitting diode when the peak wavelength has an intensity value greater than a predetermined saturation value associated with the spectrometer.

11. The aqueous solution constituent analyzer of claim 10, wherein determining the usable number of the plurality of wavelengths includes calculating a relative uncertainty value for each of the plurality of wavelengths by dividing the intensity value for each of the plurality of wavelengths by a predetermined uncertainty value associated with the spectrometer and comparing the relative uncertainty value with the predetermined relative uncertainty threshold.

12. The aqueous solution constituent analyzer of claim 10, further comprising instructions for increasing the current level to the light emitting diode when the peak wavelength has an intensity value less than the predetermined saturation value divided by a selected factor.

13. The aqueous solution constituent analyzer of claim 10, wherein the calculating includes using the Beer-Lambert equation.

14. The aqueous solution constituent analyzer of claim 10, further comprising a fiber optic cable extending from proximate the sample region to the spectrometer.

15. The aqueous solution constituent analyzer of claim 10, wherein the constituent of interest comprises nitrate.

16. A method for operating an aqueous solution constituent analyzer, comprising:

transmitting light through an aqueous solution and into a spectrometer;

receiving radiant flux data for each of a plurality of wavelengths from the spectrometer;

determining, based on the radiant flux data, a usable number of the plurality of wavelengths that satisfies a predetermined relative uncertainty threshold;

increasing the intensity of the transmitted light when the usable number of wavelengths is less than a minimum usable wavelength threshold; and calculating a concentration of a dissolved constituent of interest in the aqueous solution when the usable number of wavelengths is greater than or equal to the minimum usable wavelength threshold.

17. The method of claim 16, wherein the transmitted light is provided by an ultraviolet light emitting diode.

18. The method of claim 16, wherein the constituent of interest comprises nitrate.

19. The method of claim 16, wherein the radiant flux data for each of the plurality of wavelengths includes data indicative of a corresponding intensity value.

20. The method of claim 19, wherein determining the usable number of the plurality of wavelengths includes calculating a relative uncertainty value for each of the plurality of wavelengths by dividing the intensity value for each of the plurality of wavelengths by a predetermined uncertainty value associated with the spectrometer and comparing the relative uncertainty value with the predetermined relative uncertainty threshold.

21. The method of claim 19, further comprising determining a peak wavelength of the plurality of wavelengths having the greatest intensity value, and decreasing the current level to the light emitting diode when the peak wavelength has an intensity value greater than a predetermined saturation value associated with the spectrometer.

22. The method of claim 21, further comprising increasing the current level to the light emitting diode when the peak wavelength has an intensity value less than the predetermined saturation value divided by a selected factor.

23. The method of claim 16, wherein the calculating includes using the Beer-Lambert equation.

* * * * *